(12) United States Patent
Kochendorfer et al.

(10) Patent No.: US 8,260,637 B2
(45) Date of Patent: Sep. 4, 2012

(54) SYSTEM AND METHOD FOR LINKING A WEB-BASED RESOURCE WITH AN ELECTRONIC MEDICAL RECORD

(75) Inventors: Karl M. Kochendorfer, Columbia, MO (US); Jared S. Coberly, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 275 days.

(21) Appl. No.: 12/572,412

(22) Filed: Oct. 2, 2009

(65) Prior Publication Data

US 2010/0094655 A1 Apr. 15, 2010

Related U.S. Application Data

(60) Provisional application No. 61/102,654, filed on Oct. 3, 2008.

(51) Int. Cl.
*G06Q 50/00* (2006.01)
(52) U.S. Cl. .............................. 705/3; 705/2
(58) Field of Classification Search .................. 705/2, 3; 715/501.1
See application file for complete search history.

(56) References Cited

U.S. PATENT DOCUMENTS

| | | | |
|---|---|---|---|
| 2002/0161795 A1* | 10/2002 | O'Rourke | 707/500 |
| 2004/0059599 A1* | 3/2004 | McIvor | 705/2 |
| 2006/0184869 A1* | 8/2006 | Tiffany | 715/501.1 |

OTHER PUBLICATIONS

Peleg et al., "Sharable representation of Clinical Guidelines in GLIF: Relationship to the Arden Syntax," J. Biomed. Inform., 34(3): 170-81 (2001).
Peleg et al., "Guideline Interchange Format 3.5 Technical Specification," InterMed Collaboratory, 1-116 (2004).

* cited by examiner

*Primary Examiner* — Luke Gilligan
(74) *Attorney, Agent, or Firm* — Barnes & Thornburg LLP

(57) ABSTRACT

A data processing system and method that, in some cases, include an EMR system and a web server. In some cases, the EMR system includes a plurality of electronic medical records for a plurality of patients. One or more of the electronic medical records may include a URL or HTTP Post message that defines a path to a web-based resource, such as a treatment algorithm or medical calculator. In some embodiments, the URL and/or HTTP Post message is constructed based on information in a patient's medical record.

17 Claims, 5 Drawing Sheets

TESTCS, DEMOTWO   DOB: 07/15/1948   MRN: 08-00-01-91-6   Home Ph: (573) 882-9046   PCP: Kochendorfer MD, Karl M   IQHealth: No
More...

DIABETES MELLITUS SUMMARY

Problem List
Arthritis (7-15.00)
Back pain (724.5)
Diabetes mellitus (250.00)
Hyperlipidemia (272.2)
Hypertension (401.1)

Allergies
PCN
aspirin
sulfa drugs

Medications
amlodipine: 5 mg Daily
atorvastatin: 20 mg Daily
chondroitin-glucosamine: Daily
glipiZIDE 5 mg: bid
lisInopril: 20 mg Daily
metformin: 1000 mg bid

Diabetes Mellitus Events

| | | | | |
|---|---|---|---|---|
| BP: | 145/92 mmHg | (02/29/08) | H 150/92 mmHg | (11/08/07) |
| Wt: | 120.000 kg (264 lbs) | (02/29/08) | 121.000 kg (266 lbs) | (11/08/07) |
| BMI: | 36 | (02/29/08) | 36 | (11/08/07) |
| Eye Exam: | 5/30/2007 | (07/01/07) | | |
| Ophthalmology: | Mason Clinic visit | (05/30/07) | | |
| Foot Exam: | normal visual exam, monofilament, normal pulses | (07/01/07) | | |
| HbA1c: | H 6.7 % | (12/10/07) | H 7.5 % | (12/01/06) |
| LDL: | 94 mg/dL | (12/10/07) | 126 mg/dL | (12/05/06) |
| Cr: | 1.1 mg/dL | (09/04/07) | 1.2 mg/dL | (09/03/07) |
| MicroAlb/Cr: | H 40.0 mcg/mg Creat | (04/14/08) | 10.0 mog/mg Creat | (05/30/07) |
| Glu: | H 125 mg/dL | (09/04/07) | H 129 mg/dL | (09/03/07) |
| K+: | 4.2 mmol/L | (09/04/07) | 4.2 mmol/L | (09/03/07) |
| Smoking Hx: | Smoker | (02/29/08) | Smoker | (11/08/07) |

Chronic Disease Algorithm
Diabetes Mellitus Type II ◄─── 400

* Calculated result, which may not be displayed in the flowsheet
Est. BMI: calculated from patient's recorded weight for this date and last documented height

FIG. 4

SYSTEM AND METHOD FOR LINKING A WEB-BASED RESOURCE WITH AN ELECTRONIC MEDICAL RECORD

RELATED APPLICATION

This application claims the benefit of U.S. Provisional Application No. 61/102,654, filed Oct. 3, 2008, the entire disclosure of which is hereby incorporated by reference.

TECHNICAL FIELD

The present invention relates generally to electronic medical records ("EMRs"); in particular, the invention relates to a system and method for linking a web-based resource with an EMR.

BACKGROUND

Healthcare providers and clinicians have little time to see and treat patients. This is especially true in a clinical setting when time allotted for patient contact is frequently 15 minutes or less. Over 125 million Americans live with at least one chronic illness. An estimated 50 million Americans have three or more chronic conditions. So clinicians and other healthcare providers will frequently address more than one problem or chronic condition during a patient encounter. There are national treatment guidelines for most chronic conditions. Yet, according to a Rand study, clinicians only provide about 55% of the recommended treatment found within these national guidelines for any given chronic condition.

The treatment of chronic conditions accounts for up to about 80% of the current U.S. healthcare expenditures. A method to link a patient's current condition with a sufficient treatment algorithm based on national guidelines and best available evidence would greatly improve decision support at the point of care. This would provide more evidence-based care in less time and reduce cost spent in the healthcare industry in the U.S.

SUMMARY

According to one aspect, the invention provides a data processing system that includes an EMR system and a web server. In some cases, the EMR system includes a plurality of electronic medical records for a plurality of patients. One or more of the electronic medical records may include a URL that defines a path to a treatment algorithm webpage. In some embodiments, the URL is constructed based on information in a patient's medical record. The web server includes a treatment algorithm webpage that is configured to display treatment guidelines for a medical condition. In some embodiments, the webpage is configured to parse the URL and customize the presentation of the treatment guidelines responsive to parsing the URL.

According to another aspect, the invention provides a computer-implemented method for assisting care of a patient. The method may include the step of identifying target data in an electronic medical record. A URL defining a path to a treatment algorithm webpage is construed. In some cases, the URL may include a portion that is indicative of the target data. A hyperlink is stored in the electronic medical record with the URL. The treatment guidelines are displayed responsive to selection of the hyperlink. In some embodiments, the treatment guidelines are customized responsive to target data in the URL.

According to another aspect, the invention provides a computer-readable medium having computer-executable instructions for performing a method. The method may include the step of identifying target data in an electronic medical record. A URL defining a path to a treatment algorithm webpage is construed. In some cases, the URL may include a portion that is indicative of the target data. A hyperlink is stored in the electronic medical record with the URL. The treatment guidelines are displayed responsive to selection of the hyperlink. In some embodiments, the treatment guidelines are enhanced responsive to target data in the URL.

Additional features and advantages of this invention will become apparent to those skilled in the art upon consideration of the following detailed description of the illustrated embodiment exemplifying the best mode of carrying out the invention as presently perceived.

BRIEF DESCRIPTION OF THE DRAWINGS

FIG. 4 is an example screen shot from an electronic medical record ("EMR") showing an example hyperlink that could be used to link with a treatment algorithm;

DETAILED DESCRIPTION

Figure 2:
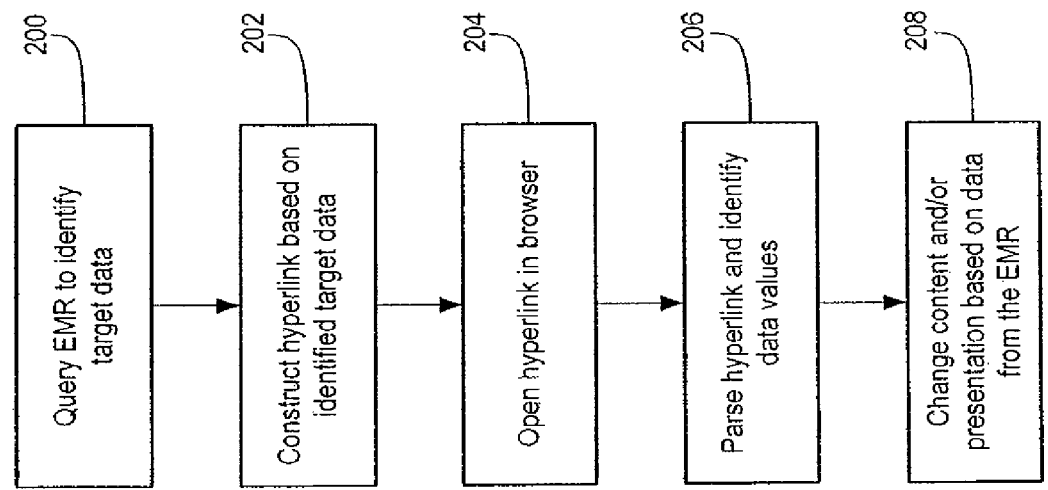
FIG. 2 is a flow chart showing example steps that may be performed during a process according to embodiment of the invention.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

According to one aspect, this disclosure provides a system and method for providing a health care provider, including but not limited to a physician, nurse, and medical assistant, with a hyperlink to a web-based treatment algorithm within a patient's electronic medical record ("EMR"). The term "hyperlink" is intended to be broadly construed to mean any navigation element that links to another document, including but not limited to embedded links, inline links, and hot areas. The hyperlink is linked to an appropriate web-based resource, such as a treatment algorithm or treatment calculator, for one of the patient's conditions based on information parsed from the patient's EMR. In some cases, the hyperlink may include information about the patient's current treatment, such as medication(s). Additional information could be included in the hyperlink, including but not limited to the patient's age, height, weight, medication dosing (Warfarin), other medications (statins) lab result (INR), targeted lab level (INRgoal), genetic profile (CYPZC9 genotype) and co-morbid condition. Embodiments are contemplated in which information in the hyperlink may be parsed by the treatment algorithm webpage to customize the visual layout or display of the webpage. For example, the webpage could highlight the current step in the treatment algorithm based on information provided in the hyperlink. Thus, the health care provider has convenient and targeted web-based resources available, which improves the quality of care.

As should be appreciated by one skilled in the art, the present invention may be embodied in many different forms, such as one or more devices, methods, data processing systems or program products. Accordingly, embodiments of the invention may take the form of an entirely software embodiment or an embodiment combining hardware and software aspects. Furthermore, embodiments of the invention may take the form of a computer program product on a computer-readable storage medium having computer-readable program code embodied in the storage medium. Any suitable storage medium may be utilized including read-only memory ("ROM"), RAM, DRAM, SDRAM, hard disks, CD-ROMs, DVD-ROMs, any optical storage device, and any magnetic storage device.

Figure 1:
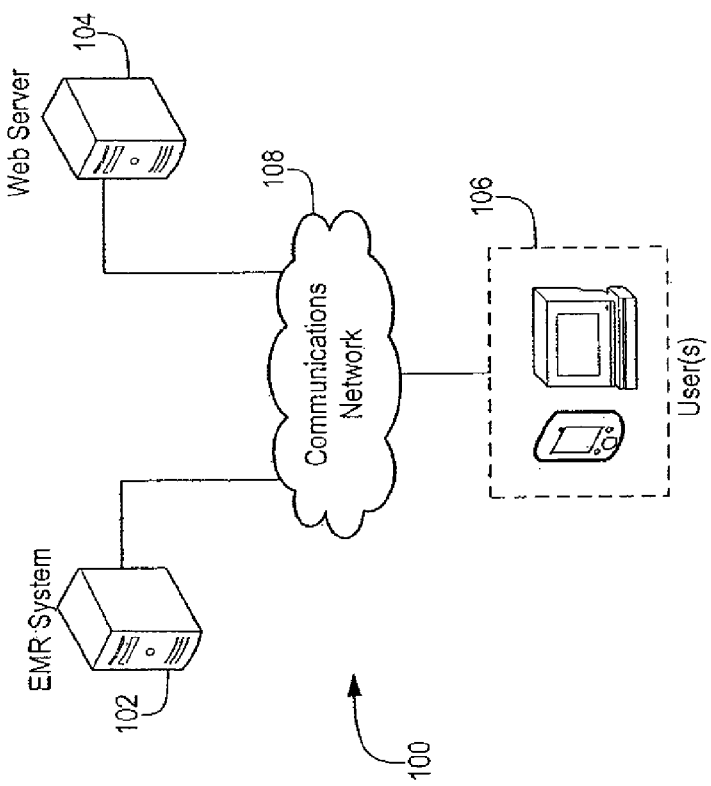
FIG. 1 is a schematic view of a data processing system according to the embodiment of the invention.

FIG. 1 shows an example data processing system 100 in accordance with one illustrative embodiment. In the illustrative embodiment shown, the data processing system 100 includes an EMR system 102, a web server 104, and one or more users 106 that exchange data and otherwise communicate using a communications network 108. Although the EMR system 102 and the web server 104 are shown by a single computing device in FIG. 1 for purposes of example, one skilled in the art should appreciate that the operation of the EMR system 102 and web server 104 may be distributed among a plurality of computing devices. For example, it should be appreciated that various subsystems (or portions of subsystems) of the EMR system 102 and/or web server 104 may operate on different computing devices.

In one embodiment, the EMR system 102 includes one or more databases with electronic medical records ("EMRs") for a plurality of patients. The EMR system 102 may provide an interface through which users 106, such as health care providers, can perform a variety of tasks, including but not limited to viewing, editing, and/or storing information relating to patients. In some embodiments, the EMR system 102 is configured to query the patient's EMR to determine whether the patient has a condition for which an appropriate web-based resource, such as a treatment algorithm, is available, including but not limited to diabetes, asthma, CAD, hypertension, high cholesterol, heart failure, atrial fibrillation, arthritis, HIV, back pain, COPD, headaches, depression, etc. Consider an example in which a web-based treatment algorithm for diabetes mellitus is available. The EMR system 102 would determine whether the patient has diabetes mellitus. If so, the EMR system 102 would construct a uniform resource locator ("URL") that defines a path to the web-based treatment algorithm for diabetes mellitus on the web server 104. For example, the EMR system 102 could construct the following URL if the patient has diabetes mellitus: www.example.com/algorithms/diabetes_mellitus.html. The hyperlink with the URL would be stored in the patient's EMR so the health care provider could quickly access the treatment algorithm by selecting the hyperlink. One skilled in the art should appreciate that a plurality of treatment algorithms could be provided for a wide variety of conditions. Moreover, other web-based resources could be used other than treatment algorithms, such as treatment calculators, including but not limited to the fracture risk assessment, Warfarin dosing and Seattle heart failure model. A patient's EMR may include zero, one, or more hyperlinks to the appropriate treatment algorithms depending on the conditions for which the patient has been diagnosed. Additionally, data parsed from the patient's chart could be passed to a web-based resource via a web service or other manner of passing the data over the communications network 108.

In some cases, the EMR system 102 may be configured to construct a hyperlink with additional information, such as information related to the patient's condition that is parsed from the patient's EMR including but not limited to medications, co-morbidities, risk factors (e.g., Framingham score), test results (e.g., FEV1, Echo), etc. For example, the EMR system 102 could be configured to determine whether the patient is taking particular medications that are associated with conditions for which the patient has been diagnosed. Consider an example in which the patient has been diagnosed with diabetes mellitus. In such an example, the EMR system 102 could determine whether the patient is taking metformin, which is a medication that is used to treat diabetes mellitus. With this information, the EMR system 102 could construct a URL with information about the medication, along with linking to the appropriate treatment algorithm. For example, the EMR system 102 could construct the following URL if the patient has diabetes mellitus and is being treated with metformin: www.example.com/algorithms/diabetes_mellitus.htm?meds=metformin. This would pass information to the web server 104 that there is a request for the treatment algorithm for diabetes mellitus, along with the current treatment for the patient. As discussed below, the treatment algorithm webpage could use this treatment information to customize the layout, display, or other qualities.

The web server 104 includes webpage(s) with treatment algorithms that could be requested by a user of the EMR system 102. The web server 102 sends the webpage that houses the requested treatment algorithm to the user 106 for viewing (and any interaction) with a browser application. The browser application could be included in the EMR system 102 or could be a third party browser application, such as Microsoft Internet Explorer or Mozilla Firefox. In some cases, the treatment algorithm webpage(s) are configured to parse the URL to customize the treatment algorithm. There could be a variety of enhancements to the treatment algorithm based on information in the URL. For example, the visual layout or display of the treatment algorithm could be changed. Consider an example in which the URL includes information about a medication being taken by the patient. In such an example, the treatment algorithm could be enhanced or customized by highlighting the step in which the medication is an appropriate treatment. One skilled in the art should appreciate that URL parsing and algorithm enhancement could occur either on the client-side or the server-side.

The user(s) 106 may access the EMR system 102 and/or web server 104 with any type of computing device via the communication network 108. By way of example, the computing devices may include but are not limited to personal computers ("PCs"), tablet computers, notebook computers, servers, personal digital assistants ("PDAs"), and cellular phones. As discussed below, the communications network 108 could communicate with users 106 using numerous protocols.

The communications network 108 may be any type of communication scheme that allows the EMR system 102, web server 104 and/or user(s) 106 to share and/or transfer data. For example, the communications network 108 may include fiber optic, wired, and/or wireless communication capability in any of a plurality of protocols, including but not limited to TCP/IP, Ethernet, WAP, IEEE 802.11, or any other protocol. Embodiments are contemplated in which some or all of the communications network 108 may be accessible through a shared public infrastructure, such as the Internet. In such embodiments, any data transmitted over the shared public infrastructure is preferably secure, if desired or as required by HIPAA. For example, the data could be encrypted, such as using a public key infrastructure ("PKI") certificate and/or secure sockets layer ("SSL"). In some embodiments, a virtual private network ("VPN") may be used. Those skilled in the art should appreciate that various other security measures could be employed in relation to transmitting data over the communications network 108.

FIG. 2 shows example steps that may be taken by the data processing system 100. The EMR system 100 identifies target data in the patient's EMR for which a web-based treatment algorithm is available (Step 200). For example, the patient's EMR may be parsed for certain elements including but not limited to a particular diagnosis, condition, and/or treatment. By way of further example, the patient's EMR could be parsed to determine whether the patient is taking certain medications. Depending on the target data that is identified, one or more hyperlinks could be constructed based on the target data (Step 202). Consider an example in which the target data is whether the patient is taking the medication metformin. In this example, the constructed hyperlink may be HTTP://www.example.com/algorithms/BM.htm?meds=metformin. The hyperlink is stored and displayed within the patient's EMR so that the health care provider may select the hyperlink to obtain helpful information that could be used for patient care. In response to the user selecting the hyperlink, the hyperlink will be opened in a browser application, as shown in step 204. The web server receives the request for a particular treatment algorithm and sends the requested webpage. The hyperlink is parsed to identify data values that may be used to enhance or customize the treatment algorithm, as shown in step 206. In some embodiments, the data values could be used to change content and/or presentation of the treatment algorithm, as shown in step 208.

Figure 3:
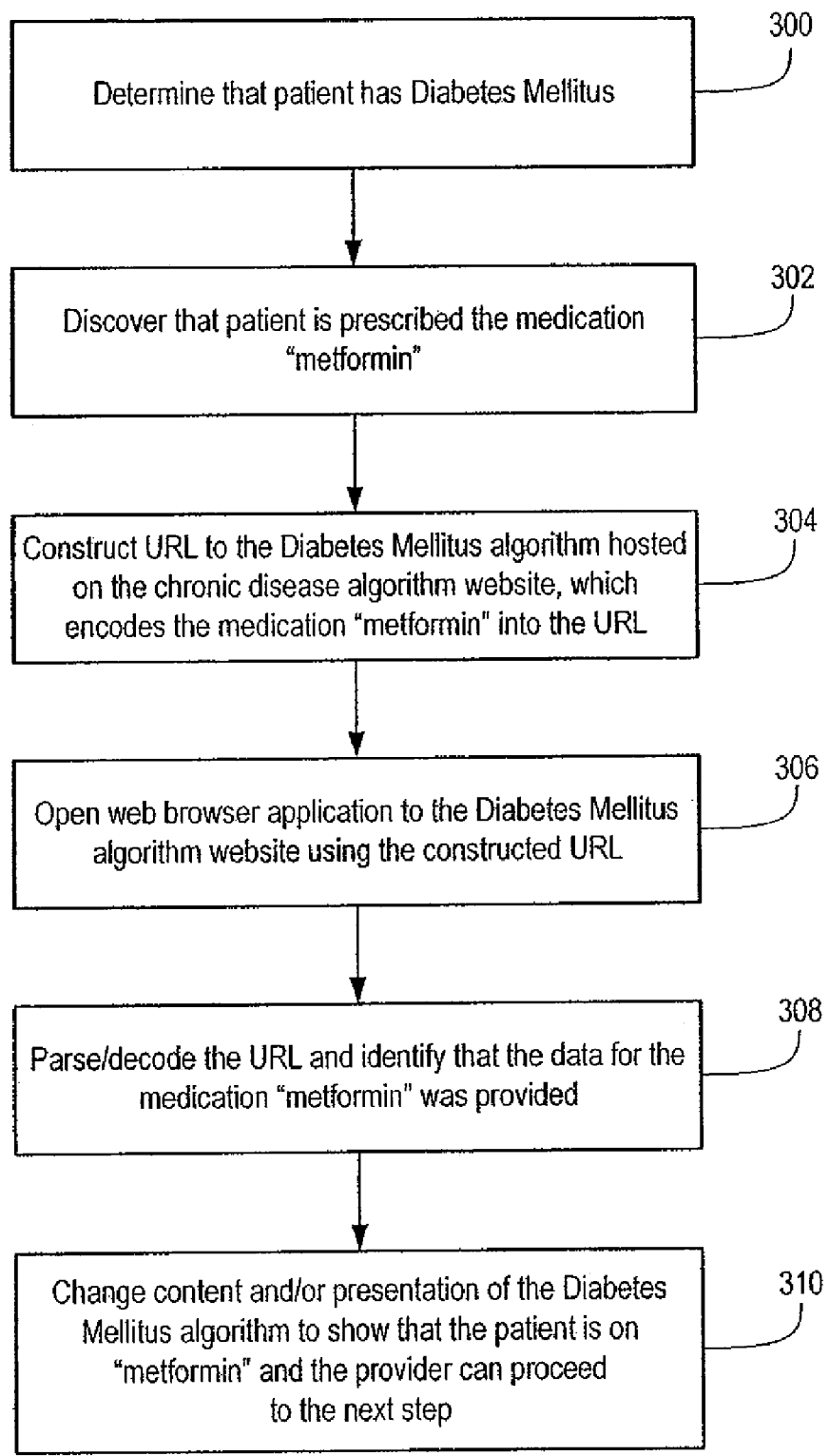
FIG. 3 is a flow chart showing example steps that may be taken based on using a medication as target information to provide a treatment algorithm.
Figure 5:
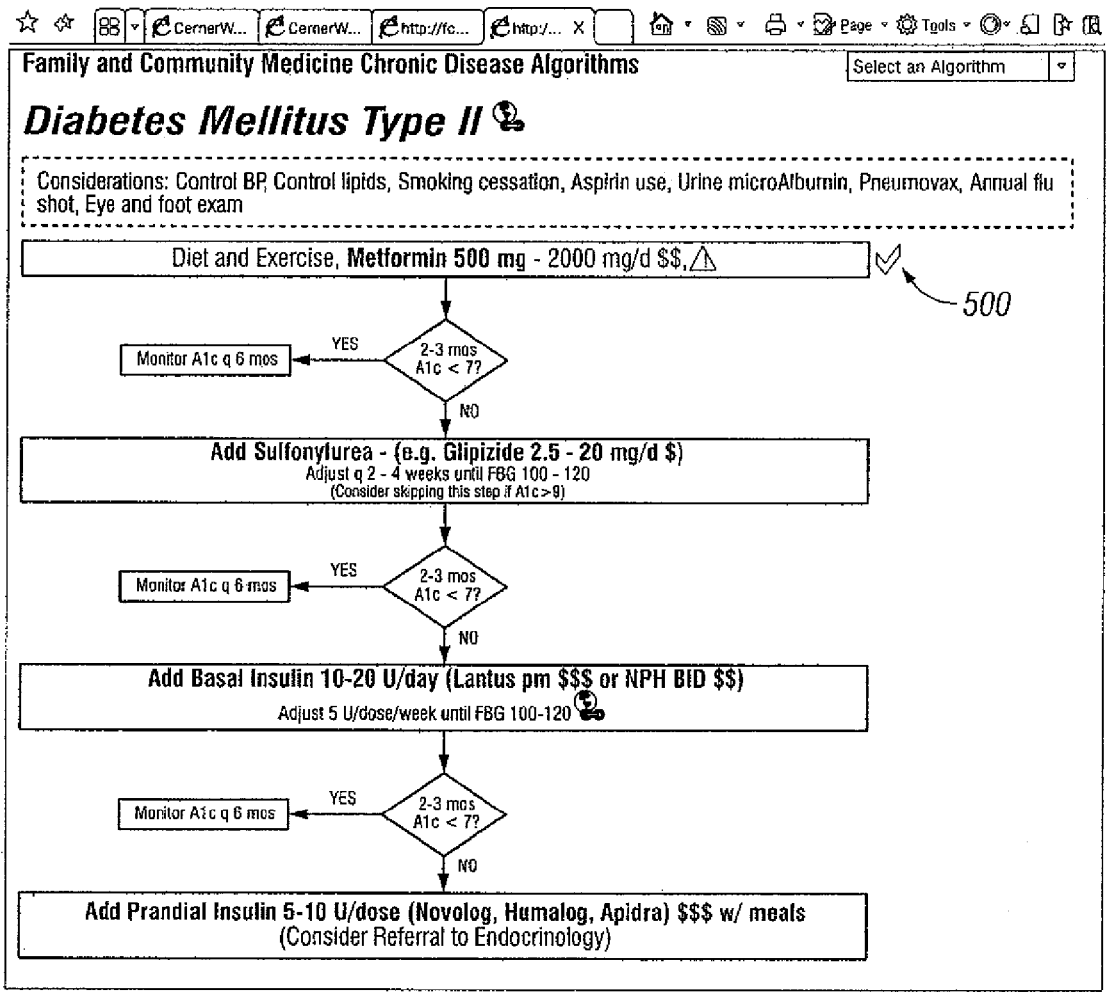
FIG. 5 is an example screen shot showing a treatment algorithm for the targeted condition with the current treatment activity highlighted.

FIGS. 3-5 show an example in which the target data includes the condition diabetes mellitus and the medication metformin. These figures are provided for example purposes only and are not intended to limit the invention in any way. In this example, the patient's EMR is queried to determine whether the patient has been diagnosed with diabetes mellitus, as shown in step 300. The patient's EMR has also been searched to determine that the patient has been prescribed the medication metformin, as shown in step 302. A hyperlink to the diabetes mellitus treatment algorithm hosted on the web server 105 is constructed which indicates the medication in the URL, as shown in step 304. FIG. 4 shows an example screen shot from the EMR system 102 regarding the diabetes mellitus summary. In this screen shot, the hyperlink 400 provides easy access to a healthcare provider regarding guidelines for treating this condition. If the user selects the hyperlink 400, a web browser application will open to the diabetes mellitus treatment algorithm webpage on the web server 104, as shown in step 306. The webpage includes code to parse the URL to identify the medication metformin, as shown in step 308. In this example, the diabetes mellitus treatment algorithm may be changed in presentation or content to show that the patient is on metformin, as shown in step 310. This allows the healthcare provider to know the next step in the algorithm guidelines that should be taken. FIG. 5 shows an example screen shot of the treatment algorithm for diabetes mellitus in which a check mark 500 is provided next to the step regarding metformin. Although a check mark is shown in FIG. 5, it should be appreciated that other manners could be used to enhance the treatment algorithm.

Figure 6:
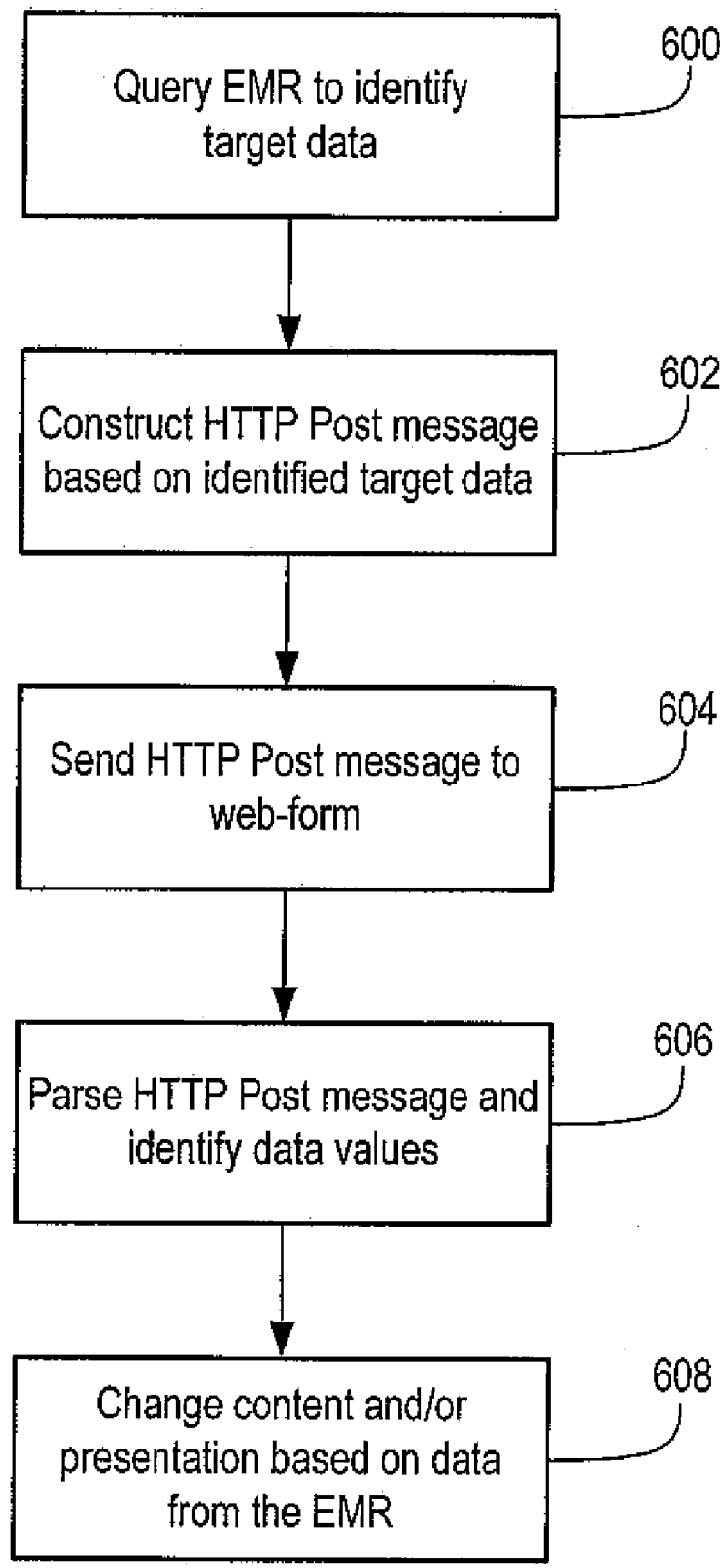
FIG. 6 is a flow chart showing example steps that may be performed during a process according to an alternative embodiment of the invention.

FIG. 6 shows example steps that may be taken by the data processing system 100 according to an alternative embodiment. In this embodiment, the EMR system 100 identifies target data in the patient's EMR for which a web-based treatment algorithm is available (Step 600). For example, the patient's EMR may be parsed for certain elements including but not limited to a particular diagnosis, condition, and/or treatment. By way of further example, the patient's EMR could be parsed to determine whether the patient is taking certain medications. Depending on the target data that is identified, one or more HTTP Post messages could be constructed based on the target data (Step 602), which could be provided to a web-based resource, such as an online web form. Consider an example in which the target data is whether the patient is taking the medication metformin. In this example, the constructed HTTP Post message may include a body of "medication: metformin." The HTTP Post message may be stored within the patient's EMR so that the health care provider may obtain helpful information that could be used for patient care. In response to user action, the HTTP Post message could be sent to the web server, which sends the requested webpage. The HTTP Post message may be parsed to identify data values that may be used to enhance or customize the treatment algorithm, as shown in step 606. In some embodiments, the data values could be used to change content and/or presentation of the treatment algorithm, as shown in step 608.

While this disclosure has been described as having an exemplary embodiment, this application is intended to cover any variations, uses, or adaptations using its general principles. It is envisioned that those skilled in the art may devise various modifications and equivalents without departing from the spirit and scope of the disclosure. Further, this application is intended to cover such departures from the present disclosure as may come within the known or customary practice within the art to which it pertains.

What is claimed is:

1. A data processing system comprising:
    an electronic medical record ("EMR") system including an EMR of a patient, wherein the EMR system is configured to construct at least one of a uniform resource locator ("URL") and HTTP Post message that is associated with the patient's EMR, wherein EMR system is configured to construct at least one of the URL and HTTP Post message to include: (i) a path to a web-based resource and (ii) medical data indicative of a medical condition of the patient that is derived from the patient's EMR, wherein the web-based resource is at least one of a treatment algorithm and a treatment calculator; and
    a web server configured to identify the web-based resource responsive to at least one of a request for the URL and a HTTP Post message, wherein the web server is configured to modify the identified web-based resource based on the medical data provided in at least one of the URL and HTTP Post message.

2. The data processing system of claim 1, wherein the web server is configured to enhance a visual appearance of the web-based resource based on the medical data provided in at least one of the URL and HTTP Post message.

3. The data processing system of claim 1, wherein the web-based resource is a treatment algorithm and the web server is configured to customize a presentation of treatment guidelines provided by the treatment algorithm responsive to the medical data provided in at least one of the URL and HTTP Post message.

4. The data processing system of claim 3, wherein the web server is configured to indicate a current step in the treatment algorithm responsive to the medical data provided in at least one of the URL and HTTP Post message.

5. The data processing system of claim 1, wherein the medical data provided in at least one of the URL and HTTP Post message includes medication data indicative of one or more medications of the patient derived from the patient's EMR and the web server is configured to customize the web-based resource based on the medication data.

6. The data processing system of claim 1, wherein the medical data provided in at least one of the URL and HTTP Post message includes dosing data indicative of medication dosing of the patient derived from the patient's EMR and the web server is configured to customize the web-based resource based on the dosing data.

7. The data processing system of claim 1, wherein the medical data provided in at least one of the URL and HTTP Post message includes treatment data indicative of a current treatment of the patient derived from the patient's EMR and the web server is configured to customize the web-based resource based on the treatment data.

8. The data processing system of claim 1, wherein the medical data provided in at least one of the URL and HTTP Post message includes lab result data indicative of a lab result of the patient derived from the patient's EMR and the web server is configured to customize the web-based resource based on the lab result data.

9. The data processing system of claim 1, wherein the medical data provided in at least one of the URL and HTTP Post message includes genetic profile data indicative of a genetic profile of the patient derived from the patient's EMR and the web server is configured to customize the web-based resource based on the genetic profile data.

10. The data processing system of claim 1, wherein the medical data provided in at least one of the URL and HTTP Post message includes co-morbid condition data indicative of a co-morbid condition of the patient derived from the patient's EMR and the web server is configured to customize the web-based resource based on the co-morbid condition data.

11. A data processing system comprising:
an electronic medical record ("EMR") system including an EMR of a patient, wherein the EMR system is configured to construct at least one uniform resource locator ("URL") that is associated with the patient's EMR, wherein EMR system is configured to construct the URL to include: (i) a path to a web-based treatment algorithm and (ii) medical data indicative of a medical condition of the patient that is derived from the patient's EMR; and
a web server configured to identify the web-based treatment algorithm responsive to a request for the URL, wherein the web server is configured to modify the presentation of treatment guidelines provided by the identified treatment algorithm responsive to the medical data provided in the URL.

12. The data processing system of claim 11, wherein the web server is configured to indicate a current step in the treatment algorithm responsive to the medical data provided in the URL.

13. A computer-implemented method for assisting care of a patient, the method comprising the steps of:
identifying target data in a patient's electronic medical record ("EMR") for which a web-based resource is available by an EMR system;
constructing at least one of a URL and HTTP Post message comprising: (a) a path to the web-based resource, and (b) data indicative of the target data;
storing a hyperlink in the patient's EMR with at least one of the URL and HTTP Post message;
presenting the web-based resource responsive to selection of the hyperlink, wherein the web-based resource is modified responsive to data indicative of the target data in at least one of the URL and HTTP Post message; and
wherein the web-based resource is one or more of: (i) a treatment algorithm, wherein the treatment algorithm provides a customized treatment guideline based on the target data in at least one of the URL and HTTP Post message; and (ii) a treatment calculator, wherein the treatment calculator provides a customized calculation based on the target data in at least one of the URL and HTTP Post message.

14. The method of claim 13, wherein a current step in the treatment guideline is provided by the treatment algorithm responsive to the target data provided in at least one of the URL and HTTP Post message.

15. The method of claim 13, wherein the target data is at least one of a medication, an age, a weight, a medication dosing, a lab result, a genetic profile, and a co-morbid condition.

16. A non-transitory computer-readable medium having computer-executable instructions for performing a method comprising:
identifying target data in an electronic medical record for which a web-based treatment algorithm is available;
constructing at least one of a URL and a HTTP Post message that includes: (i) a medical data portion indicative of the target data and (ii) a path to the web-based treatment algorithm;
storing a hyperlink in the electronic medical record with at least one of the URL and HTTP Post;
presenting treatment guidelines responsive to selection of the hyperlink, wherein the presentation of treatment guidelines is modified responsive to the medical data portion in at least one of the URL and the HTTP Post message; and
wherein the treatment algorithm enhances a visual presentation of the treatment guidelines responsive to the medical data portion provided in the URL.

17. The computer-readable medium of claim 16, wherein the treatment algorithm is configured to indicate a current step in the treatment algorithm responsive to the medical data portion provided in the URL.

* * * * *